(12) United States Patent
De Francesco et al.

(10) Patent No.: US 6,383,768 B1
(45) Date of Patent: May 7, 2002

(54) METHOD FOR PRODUCING IN VITRO THE RNA-DEPENDENT RNA POLYMERASE AND TERMINAL NUCLEOTIDYL TRANSFERASE ACTIVITIES ENCODED BY HEPATITIS C VIRUS (HCV)

(75) Inventors: Raffaele De Francesco; Licia Tomei, both of Rome (IT); Sven-Erik Behrens, Weimar (DE)

(73) Assignee: Istituto di Ricerehe di Biologia Molecolare P. Angeletti S.p.A., Pomezia (IT)

(*) Notice: Subject to any disclaimer, the term of this patent is extended or adjusted under 35 U.S.C. 154(b) by 0 days.

(21) Appl. No.: 08/952,981

(22) PCT Filed: May 24, 1996

(86) PCT No.: PCT/IT96/00106

§ 371 Date: Mar. 23, 1998

§ 102(e) Date: Mar. 23, 1998

(87) PCT Pub. No.: WO96/37619

PCT Pub. Date: Nov. 28, 1996

(30) Foreign Application Priority Data

May 25, 1995 (IT) ........................................ RM95A0343

(51) Int. Cl.[7] ............................. C12Q 1/48; C12Q 1/68; C12N 9/12
(52) U.S. Cl. ............................. 435/15; 435/194; 435/6; 435/5; 435/91.3
(58) Field of Search ............................. 435/6, 15, 194, 435/5, 91.3

(56) References Cited

U.S. PATENT DOCUMENTS 5,981,247 A 11/1999 Hagedorn et al. .......... 435/194

OTHER PUBLICATIONS

Bartholomeusz et al., Use of a Flavivirus RNA–dependent RNA polymerase assay to investigate the antiviral activity of selected compounds, 1994, pp. 341–350, vol. 24, Antiviral Research.

Grun et al., Dissociation of NS5 from Cell Fractions Containing West Nile Virus–Specific Polymerase Activity, 1987, pp. 3641–3644, vol. 61, No. 11, Journal of Virology.

Chu et al., Characterization of Kunjin Virus RNA–Dependent RNA Polymerase: Reinitiation of Synthesis in Vitro, 1987, pp. 330–337, vol. 157, Virology.

Grun et al., Characterization of West Nile Virus RNA–Dependent RNA Polymerase and Cellular Terminal Adenylyl and Uridylyl Transferase in Cell–Free Extracts, 1986, pp. 1113–1124, vol. 60, No. 3, Journal of Virology.

Bartholomeusz et al., Synthesis of dengue virus RNA in vitro: initiation and the involvment of proteins NS3 and NS5, 1993, pp. 111–121, vol. 128, Arch Virol.

Lohmann et al., Biochemical Properties of Hepatitis C Virus NS5B RNA–Dependent RNA Polymerase and Identification of Amino Acid Sequence Motifs Essential for Enzymatic Activity, 1997, pp. 8416–8428, vol. 71, No. 11, Journal of Virology.

Al et al. Expression and Characterization of the NS5B (RNA–Dependent RNA Polymerase) Gene of Hepatitis C Virus, Hepatology, 22 (4 part 2):331A, Oct. 1995.*

Tomei et al. (1993) NS3 is a serine protease required for processing of Hepatitis C Virus polyprotein. Journal of Virology 67(7): 4017–4026, Jul. 1993.*

* cited by examiner

Primary Examiner—Rebecca E. Prouty
Assistant Examiner—Richard Hutson
(74) Attorney, Agent, or Firm—Sheldon O. Heber; Jack L. Tribble

(57) ABSTRACT

This is a method for reproducing in vitro the RNA-dependent RNA polymerase activity associated with hepatitis C virus. The method is characterized in that sequences contained in NS5B are used in the reaction mixture. The terminal nucleotidyl transferase activity, a further property of the NS5B protein, can also be reproduced using this method. The method takes advantage of the fact that the NS5B protein, either purified to apparent homogeneity or present in extracts of overproducing organisms, can catalyze the addition of ribonucleotides to the 3'-termini of exogenous or endogenous RNA molecules. The invention also relates to a composition of matter that comprises sequences contained in NS5B, and to the use of these compositions for the set up of an enzymatic test capable of selecting, for therapeutic purposes, compounds that inhibit the enzymatic activity associated with NS5B.

15 Claims, 3 Drawing Sheets

METHOD FOR PRODUCING IN VITRO THE RNA-DEPENDENT RNA POLYMERASE AND TERMINAL NUCLEOTIDYL TRANSFERASE ACTIVITIES ENCODED BY HEPATITIS C VIRUS (HCV)

DESCRIPTION

The present invention relates to the molecular biology and virology of the hepatitis C virus (HCV). More specifically, this invention has as its object the RNA-dependent RNA polymerase (RdRp) and the nucleotidyl terminal transferase (TNTase) activities produced by HCV, methods of expression of the HCV RdRp and TNTase, methods for assaying in vitro the RdRp and TNTase activities encoded by HCV in order to identify, for therapeutic purposes, compounds that inhibit these enzymatic activities and therefore might interfere with the replication of the HCV virus.

As is known, the hepatitis C virus (HCV) is the main etiological agent of non-A, non-B hepatitis (NANB). It is estimated that HCV causes at least 90% of post-transfusional NANB viral hepatitis and 50% of sporadic NANB hepatitis. Although great progress has been made in the selection of blood donors and in the immunological characterization of blood used for transfusions, there is still a high number of HCV infections among those receiving blood transfusions (one million or more infections every year throughout the world). Approximately 50% of HCV-infected individuals develop cirrhosis of the liver within a period that can range from 5 to 40 years. Furthermore, recent clinical studies suggest that there is a correlation between chronic HCV infection and the development of hepatocellular carcinoma.

HCV is an enveloped virus containing an RNA positive genome of approximately 9.4 kb. This virus is a member of the Flaviviridae family, the other embers of which are the flaviviruses and the pestiviruses. The RNA genome of HCV has recently been mapped. Comparison of sequences from the HCV genomes isolated in various parts of the world has shown that these sequences can be extremely heterogeneous. The majority of the HCV genome is occupied by an open reading frame (ORF) that can vary between 9030 and 9099 nucleotides. This ORF codes for a single viral polyprotein, the length of which can vary from 3010 to 3033 amino acids. During the viral infection cycle, the polyprotein is proteolytically processed into the individual gene products necessary for replication of the virus. The genes coding for HCV structural proteins are located at the 5'-end of the ORF, whereas the region coding for the non-structural proteins occupies the rest of the ORF.

The structural proteins consist of C (core, 21 kDa), E1 (envelope, gp37) and E2 (NS1, gp61). C is a non-glycosylated protein of 21 kDa which probably forms the viral nucleocapsid. The protein E1 is a glycoprotein of approximately 37 kDa, which is believed to be a structural protein for the outer viral envelope. E2, another membrane glycoprotein of 61 kDa, is probably a second structural protein in the outer envelope of the virus.

The non-structural region starts with NS2 (p24), a hydrophobic protein of 24 kDa whose function is unknown. NS3, a protein of 68 kDa which follows NS2 in the polyprotein, is predicted to have two functional domains: a serine protease domain in the first 200 amino-terminal amino acids, and an RNA-dependent ATPase domain at the carboxy terminus. The gene region corresponding to NS4 codes for NS4A (p6) and NS4B (p26), two hydrophobic proteins of 6 and 26 kDa, respectively, whose functions have not yet been clarified. The gene corresponding to NS5 also codes for two proteins, NS5A (p56) and NS5B. (p65), of 56 and 65 kDa, respectively.

Various molecular biological studies indicate that the signal peptidase, a protease associated with the endoplasmic reticulum of the host cell, is responsible for proteolytic processing in the non-structural region, that is to say at sites C/E1, E1/E2 and E2/NS2. A virally-encoded protease activity of HCV appears to be responsible for the cleavage between NS2 and NS3. This protease activity is contained in a region comprising both part of NS2 and the part of NS3 containing the serine protease domain, but does not use the same catalytic mechanism. The serine protease contained in NS3 is responsible for cleavage at the junctions between S3 and NS4A, between NS4A and NS4B, between NS4B and NS5A and between NS5A and NS5B.

Similarly to other (+)-strand RNA viruses, the replication of HCV is thought to proceed via the initial synthesis of a complementary (−)-RNA strand, which serves, in turn, as template for the production of progeny (+)-strand RNA molecules. An RNA-dependent RNA polymerase (RdRp) has been postulated to be involved in both these steps. An amino acid sequence present in all the RNA-dependent RNA polymerases can be recognized within the NS5 region. This suggests that the NS5 region contains components of the viral replication machinery. Virally-encoded polymerases have traditionally been considered important targets for inhibition by antiviral compounds. In the specific case of HCV, the search for such substances has, however, been severely hindered by the lack of both a suitable model system of viral infection (e.g. infection of cells in culture or a facile animal model), and a functional RdRp enzymatic assay.

It has now been unexpectedly found that this important limitation can be overcome by adopting the method according to the present invention, which also gives additional advantages that will be evident from the following.

The present invention has as its object a method for reproducing in vitro the RNA-dependent RNA polymerase activity of HCV that makes use of sequences contained in the HCV NS5B protein. The terminal nucleotidyl transferase activity, a further property of the NS5B protein, can also be reproduced using this method. The method takes advantage of the fact that the proteins containing sequences of NS5B can be expressed in either eukaryotic or prokaryotic heterologous systems: the recombinant proteins containing sequences of NS5B, either purified to apparent homogeneity or present in extracts of overproducing organisms, can catalyse the addition of ribonucleotides to the 3'-termini of exogenous RNA molecules, either in a template-dependent (RdRp) or template-independent (TNTase) fashion.

The invention also extends to a new composition of matter, characterized in that it comprises proteins whose sequences are described in SEQ ID NO: 1 or sequences contained therein or derived therefrom. It is understood that this sequence may vary in different HCV isolates, as all the RNA viruses show a high degree of variability. This new composition of matter has the RdRp activity necessary to the HCV virus in order to replicate its genome.

The present invention also has as its object the use of this composition of matter in order to prepare an enzymatic assay capable of identifying, for therapeutic purposes, compounds that inhibit the enzymatic activities associated with NS5B, including inhibitors of the RdRp and that of the TNTase.

Up to this point a general description has been given of the present invention. With the aid of the following examples, a more detailed description of specific embodiments thereof will now be given, in order to give a clearer understanding of its objects, characteristics, advantages and method of operation.

Figure 3:
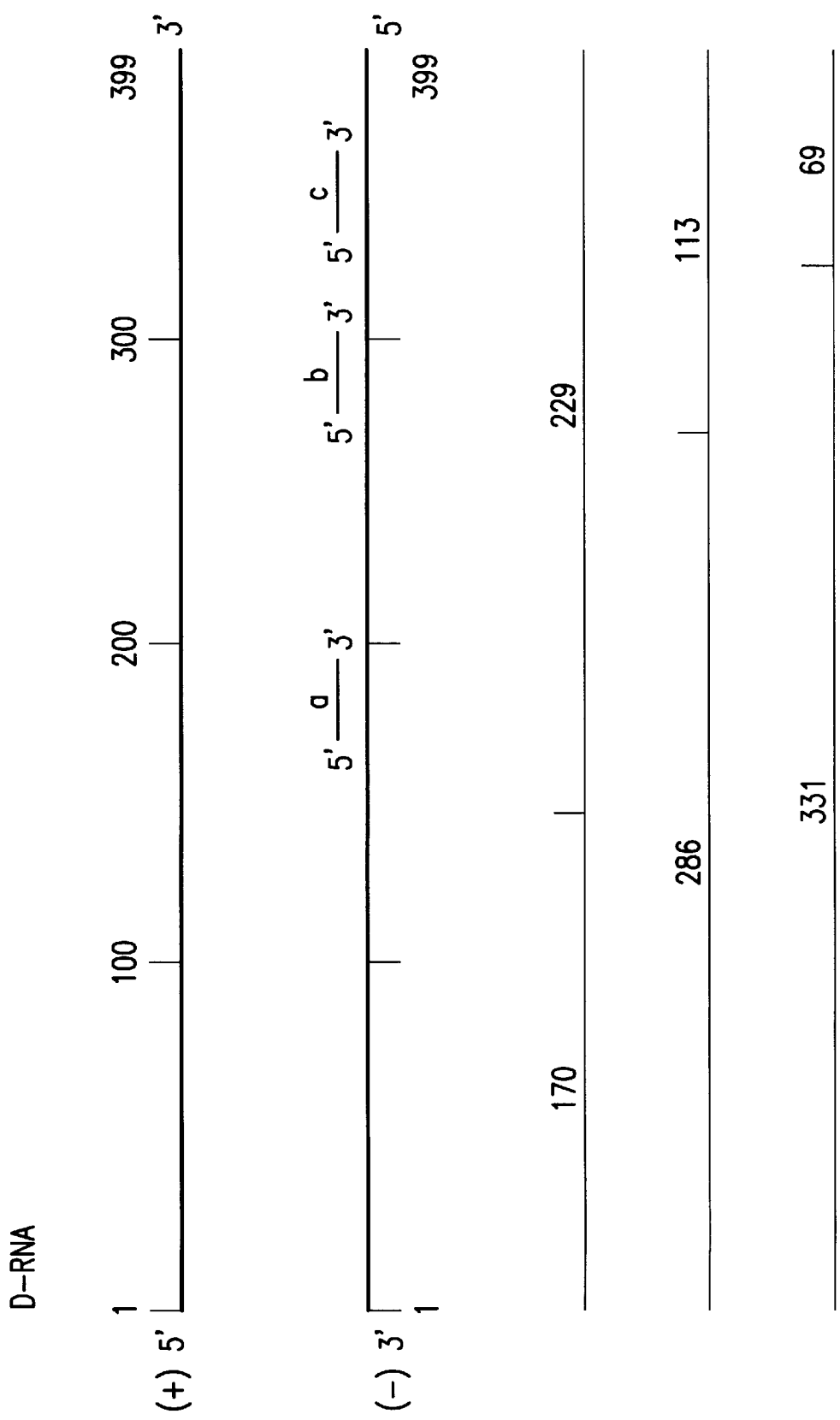

FIG. 3 shows a schematic drawing of (+) and (−) strands of D-RNA. The transcript contains the coding region of the DCoH mRNA. The DNA-oligonucleotides a, b and c were designed to anneal with the newly-synthesized antisense RNA and the DNA/RNA hybrid was subjected to cleavage with RNase H. The lower part of the scheme depicts the expected RNA fragment sizes generated by RNase digestion of the RNA (−) hybrid with oligonucleotides a, b and c, respectively.

DEPOSITS

E. Coli DH1 bacteria, transformed using the plasmids pBac 5B, pBac 25, pT7.7 DCoH and pT7.7NS5B—containing SEQ ID NO:1; SEQ ID NO:2; the cDNA for transcription of SEQ ID NO:12; and SEQ ID NO:1, respectively, filed on May 9, 1995 with The National Collections of Industrial and Marine Bacteria Ltd. (NCIMB), Aberdeen, Scotland, UK. under access numbers NCIMB 40727, 40728, 40729 and 40730, respectively.

EXAMPLE 1

Method of Expression of HCV RdRp/TNTase in Spodoptera frugiperda Clone 9 (Sf9) Cultured Cells Systems for expression of foreign genes in insect cultured cells, such as Spodoptera frugiperda clone 9 (Sf9) cells infected with baculovirus vectors are known in the art (V. A. Luckow, Baculovirus systems for the expression of human gene products, (1993) Current Opinion in Biotechnology 4, pp. 564–572). Heterologous genes are usually placed under the control of the strong polyhedrin promoter of the Autographa californica nuclear polyhedrosis virus of the Bombix mori nuclear polyhedrosis virus. Methods for the introduction of heterologous DNA in the desired site in the baculoviral vectors by homologous recombination are also known in the art (D. R. O'Reilly, L. K. Miller, V. A. Luckow, (1992), Baculovirus Expression Vectors-A Laboratory Manual, W. H. Freeman and Company, New York).

Figure 1:
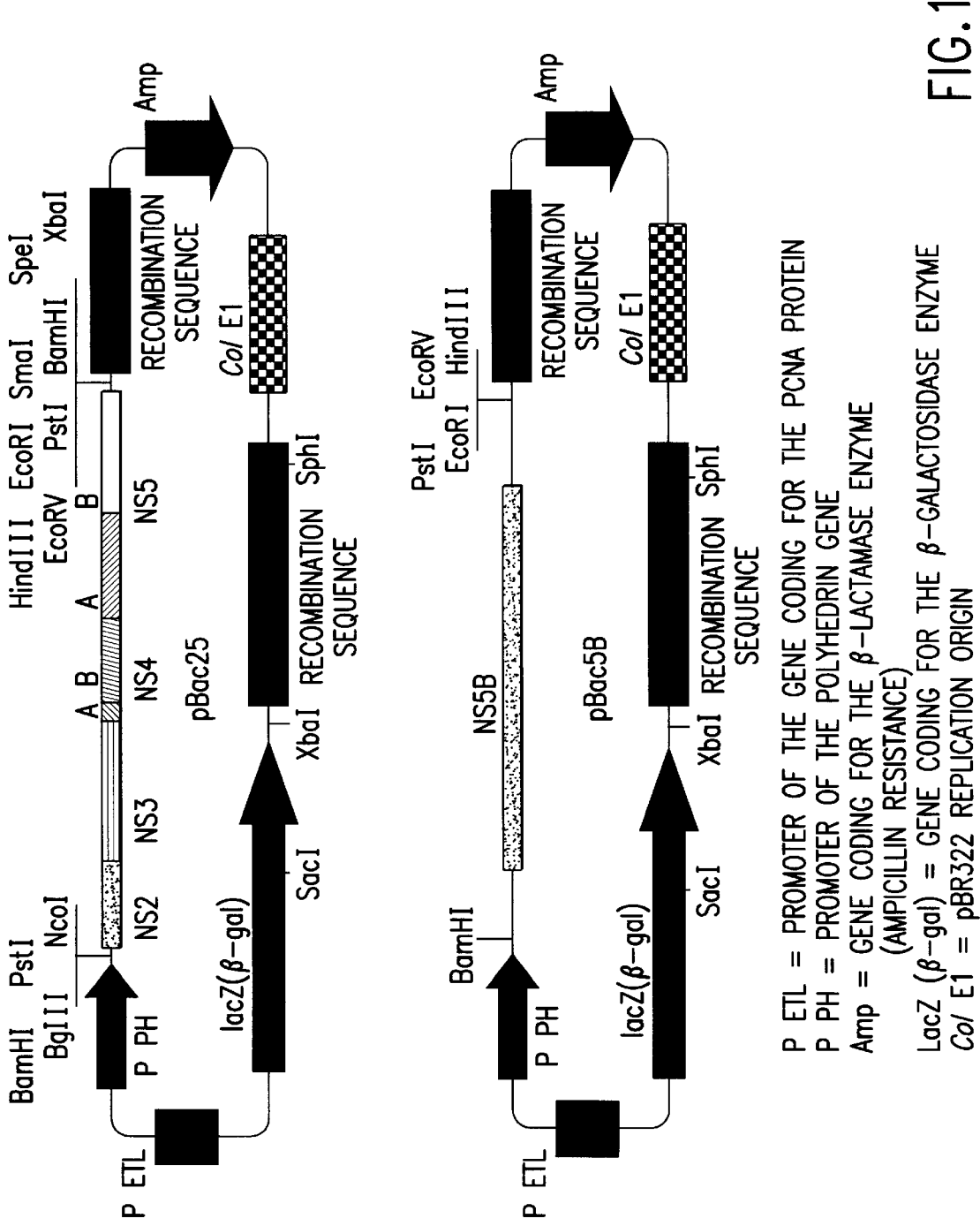
FIG. 1 shows the plasmids constructs used for the transfer of HCV cDNA into a baculovirus expression vector.

Plasmid vectors pBac5B and pBac25 are derivatives of a derivative of pBlueBacIII (Invitrogen) and were constructed for transfer of genes coding for NS4B and other non-structural HCV proteins in baculovirus expression vectors. The plasmids are schematically illustrated in FIG. 1 and their construction is described in detail in Example 8. Selected fragments of the cDNA corresponding to the genome of the HCV-BK isolate (HCV-BK; Takamizawa, A., Mori, C., Fuke, I., Manabe, S., Murakami, S., Fujita, J., Onishi, E., Andoh, T., Yoshida, I. and Okayama, H., (1991) Structure and Organization of the Hepatitis C Virus Genome Isolated from Human Carriers J. Virol., 65, 1105–1113) were cloned under the strong polyhedrin promoter of the nuclear polyhedrosis virus and flanked by sequences that allowed homologous recombination in a baculovirus vector.

In order to construct pBac5B, a PCR product containing the cDNA region encoding amino acids 2420 to 3010 of the HCV polyprotein and corresponding to the NS5B protein (SEQ ID NO:1) was cloned between the BamHI and HindIII sites of pBlue BacIII. The PCR sense oligonucleotide contained a translation initiation signal, whereas the original HCV termination codon serves for translation termination.

pBac25 is a derivative of pBlueBacIII (Invitrogen) where the cDNA region coding for amino acids 810 to 3010 of the HCV-BK polyprotein (SEQ ID NO:2) was cloned between the NcoI and the HindIII restriction sites.

Spodoptera frugiperda clone 9 (Sf9) cells and baculovirus recombination kits were purchased from Invitrogen. Cells were grown on dishes or in suspension at 27° C. in complete Grace's insect medium (Gibco) containing 10% foetal bovine serum (Gibco). Transfection, recombination, and selection of baculovirus constructs were performed as recommended by the manufacturer. Two recombinant baculovirus clones, Bac25 and Bac5B, were isolated that contained the desired HCV cDNA.

For protein expression, Sf9 cells were infected either with the recombinant baculovirus Bac25 or Bac5B at a density of $2 \times 10^6$ cells per ml in a ratio of about 5 virus particles per cell. 48–72 hours after infection, the Sf9 cells were pelleted, washed once with phosphate buffered saline (PBS) and carefully resuspended ($7.5 \times 10^7$ cells per ml) in buffer A (10 mM Tris/Cl pH 8, 1.5 mM $MgCl_2$, 10 mM NaCl) containing 1 mM dithiothreitol (DTT), 1 mM phenylmethylsulphonyl-fluoride (PMSF, Sigma) and 4 mg/ml leupeptin. All the following steps were performed on ice: after swelling for 30 minutes, the cells were disrupted by 20 strokes in a Dounce homogeniser using a tight-fitting pestle. Glycerol, as well as the detergents Nonidet P-40 (NP40) and 3-[(3-Cholamidopropyl)-dimethyl-ammonio]-1-propanesulfonate (CHAPS), were added to final concentrations of 10% (v/v), 1% (v/v) and 0.5% /w/v), respectively, and the cellular extract was incubated for a further hour on ice with occasional agitation. The nuclei were pelleted by centrifugation for 10 minutes at 1000×g, and the supernatant was collected. The pellet was resuspended in buffer A containing the above concentrations of glycerol and detergents (0.5 ml per 7.5× $10^7$ nuclei) by 20 strokes in the Dounce homogeniser and then incubated for one hour on ice. After repelleting the nuclei, both supernatants were combined, centrifuged for 10 minutes at 8000×g and the pellet was discarded. The resulting crude cytoplasmic extract was used either directly to determine the RdRp activity or further purified on a sucrose gradient (see Example 5).

Infection of Sf9 cells with either the recombinant baculovirus Bac25 or Bac5B leads to the expression of the expected HCV proteins. Indeed, following infection of Sf9 cells with Bac25, correctly-processed HCV NS2 (24 kDa), NS3 (68 kDa), NS4B (26 kDa), NS4A (6 kDa), NS5A (56 kDa) and NS5B (65 kDa) proteins can be detected in the cell lysates by SDS-polyacrylamide gel electrophoresis (SDS-PAGE) and immunostaining. Following infection of Sf9 cells with Bac5B, only one HCV-encoded protein, corresponding in size to authentic NS5B (65 kDa), is detected by SDS-PAGE followed by immuno- or Coomassie Blue staining.

EXAMPLE 2

Method of Assay of Recombinant HCV RdRp on a Synthetic RNA Template/Substrate

The RdRp assay is based on the detection of labelled nucleotides incorporated into novel RNA products. The in vitro assay to determine RdRp activity was performed in a total volume of 40 μl containing 1–5 μl of either Sf9 crude cytoplasmic extract or purified protein fraction. Unfractionated or purified cytoplasmic extracts of Sf9 cells infected with Bac25 or Bac5B may be used as the source of HCV RdRp. A Sf9 cell extract obtained from cells infected with a recombinant baculovirus construct expressing a protein that is not related to HCV may be used as a negative control. The following supplements are added to the reaction mixture (final concentrations): 20 mM Tris/Cl pH 7.5, 5 mM $MgCl_2$, 1 mM DTT, 25 mM KCl, 1 mM EDTA, 5–10 μCi [$^{32}$P] NTP of one species (unless otherwise specified, GTP, 3000 Ci/mmol, Amersham, was used), 0.5 mM each NTP (i.e. CTP, UTP, ATP unless specified otherwise), 20 U RNasin (Promega), 0.5 μg RNA-substrate (ca. 4 pmol; final concentration 100 nM), 2 μg actinomycin D (Sigma). The reaction was incubated for two hours at room temperature, stopped by the addition of an equal volume of 2×Proteinase K (PK, Boehringer Mannheim) buffer (300 mM NaCl, 100 mM Tris/Cl pH 7.5, 1% w/v SDS) and followed by half an hour of treatment with 50 μg of PK at 37° C. RNA products were PCA extracted, precipitated with ethanol and analysed by electrophoresis on 5% polyacrylamide gels containing 7M urea.

The RNA substrate we normally used for the assay (D-RNA) had the sequence reported in SEQ ID NO: 12, and was typically obtained by in vitro transcription of the linearized plasmid pT7-7(DCoH) with T7 polymerase, as described below.

Plasmid pT7-7(DCoH) (FIG. 2) was linearized with the unique BglII restriction site contained at the end of the DCoH coding sequence and transcribed in vitro with T7 polymerase (Stratagene) using the procedure described by the manufacturer. Transcription was stopped by the addition of 5 U/10 μl of DNaseI (Promega). The mixture was incubated for a further 15 minutes and extracted with phenol/chloroform/isoamylalcohol (PCA). Unincorporated nucleotides were removed by gel-filtration through a 1-ml Sephadex G50 spun column. After extraction with PCA and ethanol precipitation, the RNA was dried, redissolved in water and its concentration determined by optical density at 260 nm.

As will be clear from the experiments described below, any other RNA molecule other than D-RNA, may be used for the RdRp assay of the invention.

The above described HCV RdRp assay gave rise to a characteristic pattern of radioactively-labelled reaction products: one labelled product, which comigrated with the substrate RNA was observed in all reactions, including the negative control. This RNA species could also be visualised by silver staining and was thus thought to correspond to the input substrate RNA, labelled most likely by terminal nucleotidyl transferase activities present in cytoplasmic extracts of baculovirus-infected Sf9 cells. In the reactions carried out with the cytoplasmic extracts of Sf9 cells infected with either Bac25 or Bac5B, but not of cells infected with a recombinant baculovirus construct expressing a protein that is not related to HCV, an additional band was observed, migrating faster than the substrate RNA. This latter reaction product was found to be labelled to a high specific activity, since it could be detected solely by autoradiography and not by silver staining. This novel product was found to be derived from the externally-added RNA template, as it was absent from control reactions where no RNA was added. Interestingly, the formation of a labelled species migrating faster than the substrate RNA was consistently observed with a variety of template RNA molecules, whether containing the HCV 3'-untranslated region or not. The 399 nucleotide mRNA of the liver-specific transcription cofactor DCoH (D-RNA) turned out to be an efficiently accepted substrate in our RdRp assay.

In order to define the nature of the novel species generated in the reaction by the Bac25- or Bac5B-infected cell extracts, we carried out the following series of experiments. (i) The product mixture was treated with RNAse A or Nuclease P1. As this resulted in the complete disappearance of the radioactive bands, we concluded that both the labelled products were RNA molecules. (ii) Omission from the reaction mixtures of any of the four nucleotide triphosphates resulted in labelling of only the input RNA, suggesting that the faster migrating species is a product of a polymerisation reaction. (iii) Omission of $Mg^{2+}$ ions from the assay caused a complete block of the reaction: neither synthesis of the novel RNA nor labelling of the input RNA were observed. (iv) When the assay was carried out with a radioactively labelled input RNA and unlabelled nucleotides, the labelled product was indistinguishable from that obtained under the standard conditions. We concluded from this result that the novel RNA product is generated from the original input RNA molecule.

Taken together, our data demonstrate that the extracts of Bac25- or Bac5B-infected Sf9 cells contain a novel magnesium-dependent enzymatic activity that catalyses de novo RNA synthesis. This activity was shown to be dependent on the presence of added RNA, but independent of an added primer or of the origin of the input RNA molecule. Moreover, as the products generated by extracts of Sf9 cells infected with either Bac25 or Bac5B appeared to be identical, the experiments just described indicate that the observed RdRp activity is encoded by the HCV NS5B protein.

EXAMPLE 3

Methods for the Characterization of the HCV RdRp RNA Product

The following methods were employed in order to elucidate the structural features of the newly-synthesized RNA product. Under our standard electrophoresis conditions (5% polyacrylamide, 7M urea), the size of the novel RNA product appeared to be approximately 200 nucleotides. This could be due to either internal initiation of RNA transcription, or to premature termination. These possibilities, however, appeared to be very unlikely, since products derived from RdRp assays using different RNA substrates were all found to migrate significantly faster than their respective templates. Increasing the temperature during electrophoresis and the concentration of acrylamide in the analytical gel lead to a significantly different migration behaviour of the RdRp product. Thus, using for instance a gel system containing 10% acrylamide, 7M urea, where separation was carried out at higher temperature, the RdRp product migrated slower than the input substrate RNA, at a position corresponding to at least double the length of the input RNA. A similar effect was observed when RNA-denaturing agents such as methylhydroxy-mercury ($CH_3HgOH$, 10 mM) were added to the RdRp products prior to electrophoresis on a low-percentage/lower temperature gel. These observations suggest that the RdRp product possesses an extensive secondary structure.

We investigated the susceptibility of the product molecule to a variety of ribonucleases of different specificity. The product was completely degraded upon treatment with RNase A. On the other hand, it was found to be surprisingly resistant to single-strand specific nuclease RNase T1. The input RNA was completely degraded after 10 minutes incubation with 60 U RNase T1 at 22° C. and silver staining of the same gel confirmed that not only the template, but also all other RNA usually detectable in the cytoplasmic extracts of Sf9 cells was completely hydrolysed during incubation with RNAse T1. In contrast, the RdRp product remained unaltered and was affected only following prolonged incubation with RNase T1. Thus, after two hours of treatment with RNase T1, the labelled product molecule could no longer be detected at its original position in the gel. Instead, a new band appeared that had an electrophoretic mobility similar to the input template RNA. A similar effect was observed when carrying out the RNAse T1 digestion for 1 hour, but at different temperatures: at 22° C., the RdRp product remained largely unaffected whereas at 37° C. it was converted to the new product that co-migrates with the original substrate.

The explanation for these observations is that the input RNA serves as a template for the HCV RdRp, where the 3'-OH is used to prime the synthesis of the complementary strand by a turn-or "copy-back" mechanism to give rise to a duplex RNA "hairpin" molecule, consisting of the sense (template) strand to which an antisense strand is covalently attached. Such a structure would explain the unusual electrophoretic mobility of the RdRp product on polyacrylamide gels as well as its high resistance to single-strand specific nucleases. The turn-around loop should not be base-paired and therefore ought to be accessible to the nucleases. Treatment with RNase T1 thus leads to the hydrolysis of the covalent link between the sense and antisense strands to yield a double-stranded RNA molecule. During denaturing gel electrophoresis the two strands become separated and only the newly-synthesized antisense strand, which should be similar in length to the original RNA template, would remain detectable. This mechanism would appear rather likely, especially in view of the fact that this kind of product is generated by several other RNA polymerases in vitro.

The following experiment was designed in order to demonstrate that the RNA product labelled during the polymerase reaction and apparently released by RNase T1 treatment exhibits antisense orientation with respect to the input template. For this purpose, we synthesized oligodeoxyribonucleotides corresponding to three separate sequences of the input template RNA molecule (FIG. 2), oligonucleotide a, corresponding to nucleotides 170–195 of D-RNA (SEQ ID NO: 3); oligonucleotide b, complementary to nucleotides 286–309 (SEQ ID NO: 4); oligonucleotide c, complementary to nucleotides 331–354 (SEQ ID NO: 5). These were used to generate DNA/RNA hybrids with the product of the polymerase reaction, such that they could be subjected to RNase H digests. Initially, the complete RdRp product was used in the hybridizations. However, as this structure is too thermostable, no specific hybrids were formed. The hairpin RNA was therefore pre-treated with RNase T1, denatured by boiling for 5 minutes and then allowed to cool down to room temperature in the presence of the respective oligonucleotide. As expected, exposure of the hybrids to RNase H yielded specific cleavage products. Oligonucleotide a-directed cleavage lead to products of about 170 and 220 nucleotides in length, oligonucleotide b yielded products of about 290 and 110 nucleotides and oligonucleotide c gave rise to fragments of about 330 and 65 nucleotides. As these fragments have the expected sizes (see FIG. 3), the results indicate that the HCV NS5B-mediated. RNA synthesis proceeds by a copy-back mechanism that generates a hairpin-like RNA duplex.

EXAMPLE 4

Method of Assay of Recombinant HCV TNTase on a Synthetic RNA Substrate

The TNTase assay is based on the detection of template-independent incorporation of labelled nucleotides to the 3' hydroxyl group of RNA substrates. The RNA substrate for the assay (D-RNA) was typically obtained by in vitro transcription of the linearized plasmid pT7-7DCOH with T7 polymerase as described in Example 2. However, any other RNA molecule, other than D-RNA, may be used for the TNTase assay of the invention.

The in vitro assay to determine TNTase activity was performed in a total volume of 40 μl containing 1–5 μl of either Sf9 crude cytoplasmic extract or purified protein fraction. Unfractionated or purified cytoplasmic extracts of Sf9 cells infected with Bac25 or Bac5B may be used as the source of HCV TNTase. An Sf9 cell extract obtained from cells infected with a recombinant baculovirus construct expressing a protein that is not related to HCV may be used as a negative control. The following supplements are added to the reaction mixture (final concentrations): 20 mM Tris/Cl pH 7.5, 5 MM $MgCl_2$, 1 mM DTT, 25 mM KCl, 1 mM EDTA, 5–10 μCi [$^{32}$P] NTP of one species (unless otherwise specified, UTP, 3000 Ci/mmol, Amersham, was used), 20 U RNasin (Promega), 0.5 μg RNA-substrate (ca. 4 pmol; final concentration 100 nM), 2 μg actinomycin D (Sigma). The reaction was incubated for two hours at room temperature, stopped by the addition of an equal volume of 2×Proteinase K (PK, Boehringer Mannheim) buffer (300 mM NaCl, 100 mM Tris/Cl pH 7.5, 1% w/v SDS) and followed by half an hour of treatment with 50 μg of PK at 37° C. RNA products were PCA extracted, precipitated with ethanol and analysed by electrophoresis on 5% polyacrylamide gels containing 7M urea.

EXAMPLE 5

Method for the Purification of the HCV RdRp/ TNTase by Sucrose Gradient Sedimentation A linear 0.3–1.5 M sucrose gradient was prepared in buffer A containing detergents (see Example 1). Up to 2 ml of extract of Sf9 cells infected with Bac5B or Bac25 (corresponding to about 8×10$^7$ cells) were loaded onto a 12 ml gradient. Centrifugation was carried out for 20 hours at 39000×g using a Beckman SW40 rotor. 0.5 ml fractions were collected and assayed for activity. The NS5B protein, identified by western blotting, was found to migrate in the density gradients with an unexpectedly high sedimentation coefficient. The viral protein and ribosomes were found to co-sediment in the same gradient fractions. This unique behaviour enabled us to separate the viral protein from the main bulk of cytoplasmic proteins, which remained on the top of the gradient. The RdRp activity assay revealed that the RdRp activity co-sedimented with the NS5B protein. A terminal nucleotidyl transferase activity (TNTase) was also present in these fractions.

EXAMPLE 6

Method for the Purification of the HCV TNTase/ RdRp From Sf9 Cells

Whole cell extracts are made from 1 g of Sf9 cells infected with Bac5B recombinant baculovirus. The frozen cells are thawed on ice in 10 ml of buffer containing 20 mM Tris/HCl pH 7.5, 1 mM EDTA, 10 mM DTT, 50% glycerol (N buffer) supplemented with 1 mM PMSF. Triton X-100 and NaCl are then added to a final concentration of 2% and 500 mM, respectively, in order to promote cell breakage. After the addition of $MgCl_2$ (10 mM) and DNase I (15 µg/ml), the mixture is stirred at room temperature for 30 minutes. The extract is then cleared by ultracentrifugation in a Beckman centrifuge, using a 90 Ti rotor at 40,000 rpm for 30 minutes at 4° C. The cleared extract is diluted with a buffer containing 20 mM Tris/HCl pH 7.5, 1 mM EDTA, 10 mM DTT, 20% glycerol, 0.5% Triton X-100 (LG buffer) in order to adjust the NaCl concentration to 300 mM and incubated batchwise with 5 ml of DEAE-Sepharose Fast Flow, equilibrated in LG buffer containing 300 mM NaCl. The matrix is then poured into a column and washed with two volumes of the same buffer. The flow-through and the first wash of the DEAE-Sepharose Fast Flow column is diluted 1:3 with LG buffer and applied onto a Heparin-Sepharose CL6B column (10 ml) equilibrated with LG buffer containing 100 mM NaCl. The Heparin-Sepharose CL6B is washed thoroughly and the bound proteins are eluted with a linear 100 ml gradient, from 100 mM to 1M NaCl in buffer LG. The fractions containing NS5B, as judged by silver- and immuno-staining of SDS-PAGE, are pooled and diluted with LG buffer in order to adjust the NaCl concentration to 50 mM. The diluted fractions are subsequently applied to a Mono Q-FPLC column (1 ml) equilibrated with LG buffer containing 50 mM NaCl. Proteins are eluted with a linear gradient (20 ml) from 50 mM to 1M NaCl in LG buffer. The fractions containing NS5B, as judged by silver- and immuno-staining of SDS-PAGE, are pooled and dialysed against LG buffer containing 100 mM NaCl. After extensive dialysis, the pooled fractions were loaded onto a PoyU-Sepharose CL6B (10 ml) equilibrated with LG buffer containing 100 mM NaCl. The PoyU-Sepharose CL6B was washed thoroughly and the bound proteins were eluted with a linear 100 ml gradient, from 100 mM to 1M NaCl in buffer LG. The fractions containing NS5B, as judged by silver- and immuno-staining of SDS-PAGE, are pooled, dialysed against LG buffer containing 100 mM NaCl and stored in liquid nitrogen prior to activity assay.

Fractions containing the purified protein NS5B were tested for the presence of both activities. The RdRp and TNTase activities were found in the same fractions. These results indicate that both activities, RNA-dependent RNA polymerase and terminal ribonucleotide transferase are the functions of the HCV NS5B protein.

We tested the purified NS5B for terminal nucleotidyl transferase activity with each of the four ribonucleotide triphosphates at non-saturating substrate concentrations. The results clearly showed that UTP is the preferred TNTase substrate, followed by ATP, CTP and GTP irrespective of the origin of the input RNA.

EXAMPLE 7

Method of Assay of Recombinant HCV RdRp on a Homopolymeric RNA Template

Thus far we have described that HCV NS5B possesses an RNA-dependent RNA polymerase activity and that the synthesis of complementary RNA strand is a template-primed reaction. Interestingly, using unfractionated cytoplasmic extracts of Bac5B or Bac25 infected Sf9 cells as a source of RdRp we were not able to observe complementary strand RNA synthesis that utilized an exogenously added oligonucleotide as a primer. We reasoned that this could be due to the abundant ATP-dependent RNA-helicases that would certainly be present in our unfractionated extracts. We therefore wanted to address this question using the purified NS5B.

First of all, we wanted to establish whether the purified NS5B polymerase is capable of synthesizing RNA in a primer-dependent fashion on a homopolymeric RNA template: such a template should not be able to form intramolecular hairpins and therefore we expected that complementary strand RNA synthesis be strictly primer-dependent. We thus measured UMP incorporation dependent on poly(A) template and evaluated both oligo(rU)$_{12}$ and oligo(dT)$_{12-18}$ as primers for the polymerase reaction. Incorporation of radioactive UMP was measured as follows. The standard reaction (10–100 µl) was carried out in a buffer containing 20 mM Tris/HCl pH 7.5, 5 mM $MgCl_2$, 1 mM DTT, 25 mM KCl, 1 mM EDTA, 20 U RNasin (Promega), 1 µCi [$^{32}$P] UTP (400 Ci/mmol, Amersham) or 1 µCi [$^{3}$H] UTP (55 Ci/mmol, Amersham), 10 µM UTP, and 10 µg/ml poly(A) or poly(A)/oligo(dT)$_{12-18}$. Oligo(U)$_{12}$ (1 µg/ml) was added a primer. Poly A and polyA/oligodT$_{12-18}$ were purchased from Pharmacia. Oligo(U)$_{12}$ was obtained from Genset. The final NS5B enzyme concentration was 10–100 nM. Under these conditions the reaction procedeed linearly for up to 3 h hours. After 2 hours of incubation at 22°, the reaction was stopped by applying the samples to DE81 filters (Whatman), the filters washed thoroughly with 1M $Na_2HPO_4/NaH_2PO_4$, pH 7.0, rinsed with water, air dried and finally the filter-bound radioactivity was measured in a scintillation β-counter. Alternatively, the in vitro-synthesized radioactive product was precipitated by 10% trichloroacetic acid with 100 µg of carrier tRNA in 0.2 M sodium pyrophosphate, collected on 0.45-µm Whatman GF/C filters, vacuum dried, and counted in scintilaltion fluid. Although some [$^{32}$P]UMP or [$^{3}$H]UMP ncorporation was detectable even in the absence of a primer and is likely to be due to the terminal nucleotidyl transferase activity associated with our purified NS5B, up to 20% of product incorporation was observed only when oligo(rU)$_{12}$ was included as primer in the reaction mixture. Unexpectedly, also oligo(dT)$_{12-18}$ could function as a primer of poly(A)-dependent poly(U) synthesis, albeit with a lower efficiency. Other template/primers suitable for measuring the RdRp activity of NS5B include poly(C)/oligo(G) or poly(C)/oligo(dG) in the presence of radioactive GTP, poly(G)/oligo(C) or poly(G)/oligo(dC) in the presence of radioactive CTP, poly(U)/oligo(A) or poly(U)/oligo(dA) in the presence of radioactive ATP, poly(I)/oligo(C) or poly(I)/oligo(dC) in the presence of radioactive CTP.

EXAMPLE 8

Method of Expression of HCV RdRp/TNTase in *E. Coli*

Figure 2:
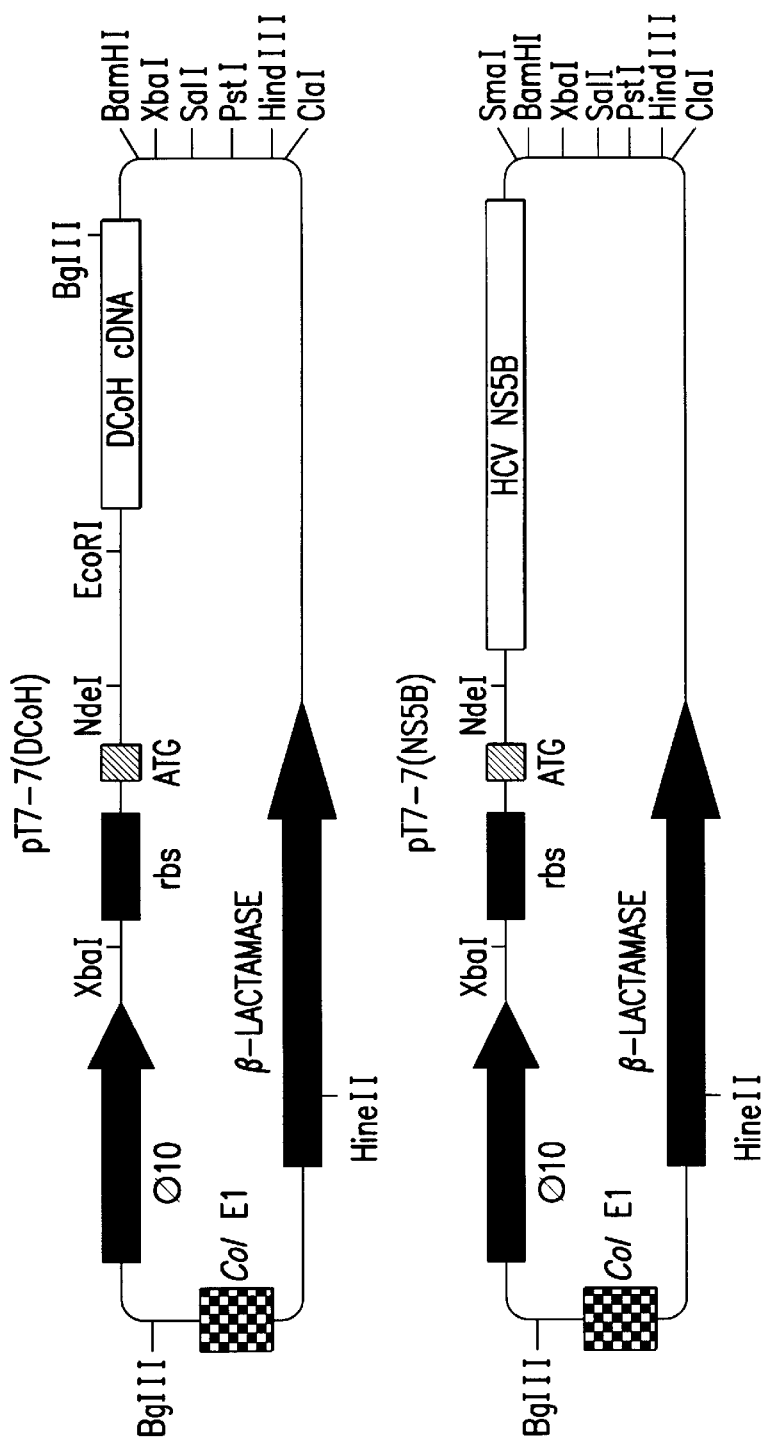
FIG. 2 shows the plasmids used for the in vitro synthesis of the D-RNA substrate of the HCV RNA-dependent RNA polymerase [pT7-7 (DCoH)], and for the expression of the HCV RNA-dependent RNA polymerase in E. coli cells [pT7-7(NS5B)], respectively.

The plasmid pT7-7(NS5B), described in FIG. 2 and Example 8, was constructed in order to allow expression in *E. coli* of the HCV protein fragment having the sequence reported in SEQ ID NO 1. Such protein fragment contains the RdRp and the TNTase of NS5B, as discussed above. The fragment of HCV cDNA coding for the NS5B protein was thus cloned downstream of the bacteriophage T7 Ø10 promoter and in frame with the first ATG codon of the phage T7 gene 10 protein, using methods that are known to the molecular biology practice and described in detail in Example 8. The pT7-7(NS5B) plasmid also contains the gene for the b-lactamase enzyme that can be used as a marker of selection of *E. coli* cells transformed with plasmid pT7-7(NS5B).

The plasmid pT7-7(NS5B) was then transformed in the *E. coli* strain BL21(DE53), which is normally employed for high-level expression of genes cloned into expression vectors containing T7 promoter. In this strain of *E. coli*, the T7 gene polymerase is carried on the bacteriophage 1 DE53, which is integrated into the chromosome of BL21 cells (Studier and Moffatt, Use of bacteriophage T7 RNA polymerase to direct selective high-level expression of cloned genes, (1986), J. Mol. Biol. 189, p. 113–130). Expression from the gene of interest is induced by addition of isopropylthiogalactoside (IPTG) to the growth medium according to a procedure that has been previously described (Studier and Moffatt, 1986). The recombinant NS5B protein fragment containing the RdRp is thus produced in the inclusion bodies of the host cells. Recombinant NS5B protein can be purified from the particulate fraction of *E. coli* BL21(DE53) extracts and refolded according to procedures that are known in the art (D. R. Thatcher and A. Hichcok, Protein folding in Biotechnology (1994) in "Mechanism of protein folding" R. H. Pain EDITOR, IRL PRESS, p.229–255). Alternatively, the recombinant NS5B protein could be produced as soluble protein by lowering the temperature of the bacterial growth media below 20° C. The soluble protein could thus be purified from lysates of *E. coli* substantially as described in Example 5.

EXAMPLE 9

Detailed Construction of the Plasmids in Figures

Selected fragments of the cDNA corresponding to the genome of the HCV-BK isolate (HCVBK) were cloned under the strong polyhedrin promoter of the nuclear polyhedrosis virus and flanked by sequences that allowed homologous recombination in a baculovirus vector.

pBac5Bcontains the HCV-BK sequence comprised between nucleotide 7590 and 9366, and codes for the NS5B protein reported in SEQ ID NO: 1. In order to obtain this plasmid, a cDNA fragment was generated by PCR using synthetic oligonucleotides having the sequences 5'-AAGGATCCATGTCAATGTCCTACACATGGAC-3' (SEQ ID NO: 6) and 5'-AATATTCGAATTCAT CGGTTGGGGAGCAGGTAGATG-3' (SEQ ID NO: 7), respectively. The PCR product was then treated with the Klenow DNA polymerase, digested at the 5'-end with BamHI, and subsequently cloned between the BamHI and SmaI sites of the Bluescript SK(+) vector. Subsequently, the cDNA fragment of interest was digested out with the restriction enzymes BamHI and HindIII and religated in the same sites of the pBlueBacIII vector (Invitrogen).

pBac25 is contains the HCV-BK cDNA region comprised between nucleotides 2759 and 9416 of and codes for amino acids 810 to 3010 of the HCV-BK polyprotein (SEQ ID NO: 2). This construct was obtained as follows. First, the 820bp cDNA fragment containing the HCV-BK sequence comprised between nucleotides 2759 and 3578 was obtained from pCD(38-9.4) (Tomei L., Failla, C., Santolini, E., De Francesco, R. and La Monica, N. (1993) NS3 is a Serine Protease Required for Processing of Hepatitis C Virus Polyprotein *J. Virol.*, 67, 4017–4026) by digestion with NcoI and cloned in the NcoI site of the pBlueBacIII vector (Invitrogen) yielding a plasmid called pBacNCO. The cDNA fragment containing the HCV-BK sequence comprised between nucleotides 1959 and 9416 was obtained from pCD(38-9.4) (Tomei et al., 1993) by digestion with NotI and XbaI and cloned in the same sites of the Bluescript SK(+) vector yielding a plasmid called pBlsNX. The cDNA fragment containing the HCV-BK sequence comprised between nucleotides 3304 and 9416 was obtained from pBlsNX by digestion with SacII and HindIII and cloned in the same sites of the pBlsNX plasmid, yielding the pBac25 plasmid.

pT7-7(DCoH) contains the entire coding region (316 nucleotides) of the rat dimerization cofactor of hepatocyte nuclear factor-1aa (DCoH; Mendel, D. B., Khavari, P. A., Conley, P. B., Graves, M. K., Hansen, L. P., Admon, A. and Crabtree, G. R. (1991) Characterization of a Cofactor that Regulates Dimerization of a Mammalian Homeodomain Protein, *Science* 254, 1762–1767; GenBank accession number: M83740). The cDNA fragment corresponding to the coding sequence for rat DCoH was amplified by PCR using the synthetic oligonucleotide Dpr1 and Dpr2 that have the sequence TGGCTGGCAAGGCACACAGGCT (SEQ ID NO: 8) and AGGCAGGGTAGATCTATGTC (SEQ ID NO: 9), respectively. The cDNA fragment thus obtained was cloned into the SmaI restriction site of the *E. coli* expression vector pT7-7. The pT7-7 expression vector is ea derivative of pBR322 that contains, in addition to the β-lactamase gene and the Col E1 orifgin of replication, the T7 polymerase promoter Ø10 and the translational start site for the T7 gene 10 protein (Tabor S. and Richerdson C. C. (1985) A bacteriophage T7 RNA polymerase/promoter system for controlled exclusive expression of specific genes, *Proc. Natl. Acad. Sci. USA* 82, 1074–1078).

pT7-7(NS5B) contains the HCV sequence from nucleotide 7590 to nucleotide 9366, and codes for the NS5B protein reported in SEQ ID NO: 1.

In order to obtain this plasmid, a cDNA fragment was generated by PCR using synthetic oligonucleotides having the sequences 5'-TCAATGTCCTACACATGGAC-3' (SEQ ID NO: 10) and 5'-GATCTCTAGATCATCGGT TGGGGAGGAGGTAGATGCC-3' (SEQ ID NO: 11), respectively. The PCR product was then treated with the Klenow DNA polymerase, and subsequently ligated in the *E. coli* expression vector pT7-7 after linearizing it with EcoRI and blunting its estremities with the Klenow DNA polymerase. Alternatively, cDNA fragment was generated by PCR using synthetic oligonucleotides having the sequences 5'-TGTCAATGTCCTACACATGG-3' (SEQ ID NO: 13) and 5'-AATATTCGAATTCATCGGTTGGGGAGCAGGTAG ATG-3' (SEQ ID NO: 14), respectively. The PCR product was then treated with the Klenow DNA polymerase, and subsequently ligated in the *E. coli* expression vector pT7-7 after linearizing it with NdeI and blunting its estremities with the Klenow DNA polymerase.

What is claimed is:

1. A method for producing in vitro the RNA-dependent RNA polymerase activity encoded by hepatitis C virus (HCV), comprising the step of incubating together HCV NS5B, ribonucleotide substrates and a RNA template, under conditions suitable to produce said RNA-dependent RNA polymerase activity, provided that said incubating takes place in vitro and said NS5B is the only HCV protein present during said incubating.

2. The method according to claim 1, wherein said NS5B has the amino acid sequence of SEQ ID NO:1.

3. The method according to claim 2, wherein said NS5B is purified.

4. The method according to claim 3, wherein said NS5B is produced from a NS2-NS3-NS4-NS5 polyprotein by means of multiple proteolytic events that occur in an organism expressing nucleic acid encoding for said NS2-NS3-NS4-NS5 polyprotein, followed by purification of said NS5B.

5. The method according to claim 3, wherein said NS5B is provided as an extract of an organism expressing nucleic acid encoding for NS5B.

6. The method according to claim 1, wherein said NS5B is purified.

7. The method according to claim 6, wherein said NS5B is produced from a NS2-NS3-NS4-NS5 polyprotein by means of multiple proteolytic events that occur in an organism expressing nucleic acid encoding for said NS2-NS3-NS4-NS5 polyprotein.

8. A method for measuring the ability of a compound to affect a hepatitis C virus (HCV) NS5B activity comprising:

(a) incubating in vitro a composition comprising HCV NS5B, ribonucleotide substrates, an RNA template, and said compound, under conditions suitable to produce NS5B RNA-dependent RNA polymerase activity, wherein said NS5B is provided to said composition from a preparation wherein said NS5B is the only HCV protein present; and (b) measuring the ability of said compound to affect said NS5B RNA-dependent RNA polymerase activity.

9. The method of claim 8, wherein said NS5B is the only HCV protein present in said composition.

10. The method of claim 9 where said step (a) is performed in the absence of an exogenously added primer complementary to said RNA substrate.

11. The method of claim 9 wherein said preparation is a cellular extract from a cell transformed with nucleic acid encoding for NS5B.

12. The method of claim 9, wherein said NS5B is purified in said preparation.

13. The method of claim 9, wherein said NS5B has the sequence of SEQ. ID. NO. 1.

14. The method of claim 9, wherein said RNA substrate is a homopolymeric template and a complementary primer is present.

15. The method of claim 8, wherein said method measures primer independent NS5B RNA-dependent RNA polymerase activity.

* * * * *